United States Patent [19]

Lombardo

[11] Patent Number: 5,124,455
[45] Date of Patent: Jun. 23, 1992

[54] OXIME-CARBAMATES AND OXIME-CARBONATES AS BRONCHODILATORS AND ANTI-INFLAMMATORY AGENTS

[75] Inventor: Louis J. Lombardo, Belle Mead, N.J.

[73] Assignee: American Home Products Corporation, New York, N.Y.

[21] Appl. No.: 564,263

[22] Filed: Aug. 8, 1990

[51] Int. Cl.$^5$ .................. C07D 215/04; C07C 69/96; C07C 271/00
[52] U.S. Cl. .................. 546/181; 560/24; 560/26; 560/32; 560/33; 560/164; 560/165; 560/249; 558/262; 564/255; 514/640; 514/641; 514/826
[58] Field of Search .......... 560/24, 26, 32, 33, 560/164, 165, 249; 558/262; 564/255; 546/181; 514/640, 641, 826

[56] References Cited

U.S. PATENT DOCUMENTS

| | | | |
|---|---|---|---|
| 3,466,316 | 9/1969 | Payne, Jr. et al. | 260/465.4 |
| 3,647,861 | 3/1972 | Buchanan | 260/481 R |
| 3,818,073 | 6/1974 | Goebel et al. | 560/165 |
| 4,475,945 | 10/1984 | Martin | 71/105 |

FOREIGN PATENT DOCUMENTS

| | | |
|---|---|---|
| 722657 | 4/1969 | Belgium . |
| 805752 | 10/1973 | Belgium . |
| 2202689 | 5/1974 | France . |

OTHER PUBLICATIONS

Sarup et al., Indian Journal of Chemistry, vol. 18B, Oct. 1979, pp. 355-358.
Wiegrebe et al., Helvetica Chimica Acta, vol. 59, No. 3, 1976, pp. 949-962.
Indian Journal of Chemistry, Sect. B., 18B(4) 335 (1979).

Primary Examiner—Jose G. Dees
Assistant Examiner—Porfirio Nazario
Attorney, Agent, or Firm—George Tarnowski

[57] ABSTRACT

There are disclosed compounds of the formula

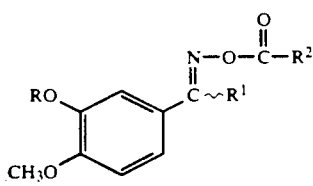

wherein
R is

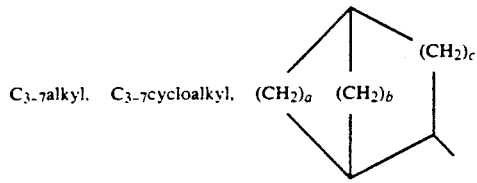

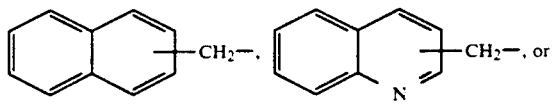

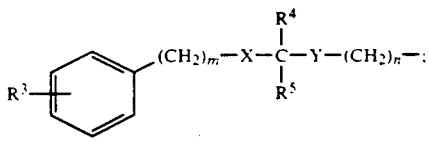

$R^1$ is hydrogen, lower alkyl or

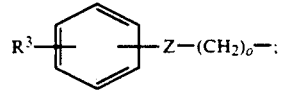

a is 1–3;
b is 1–3;
c is 0–2;
X, Y and Z are each, independently, a bond, O, S, or NH, with the proviso that if one of X or Y is O, S or NH, the other must be a bond;
$R^2$ is amino, loweralkylamino, arylamino, loweralkoxy or aryloxy;
$R^3$ is hydrogen, halo, hydroxy, lower alkoxy, aryloxy, loweralkanoyloxy, amino, lower alkylamino, arylamino or loweralkanoylamino;
$R^4$ and $R^5$ are each, independently hydrogen or lower alkyl;
m is 0–4;
n is 1–4; and
o is 1–4;

and, which by virtue of their ability to selectively inhibit an isoenzyme of 3':5'-cyclic AMP phosphodiesterase located in pulmonary smooth muscle tissue and inflammatory cells, are bronchodilatory and antinflammatory and so are useful in the treatment of acute and chronic bronchial asthma and associated pathologies.

14 Claims, No Drawings

OXIME-CARBAMATES AND OXIME-CARBONATES AS BRONCHODILATORS AND ANTI-INFLAMMATORY AGENTS

This invention relates to novel aryl oxime-carbamates and carbonates having bronchodilatory and anti-inflammatory activities and being useful in the treatment of asthma.

Asthma is a disease in which respiratory distress is produced as a result of airway narrowing. This narrowing is caused largely by 1) the acute constriction of the respiratory smooth muscle that surrounds the airways and 2) chronic inflammation within the lung. Agents that reverse bronchospasm and prevent pulmonary inflammation are thus useful in the relief of the symptoms of asthma.

One approach for reversing bronchospasm and also inhibiting inflammation is to elevate intracellular adenosine cyclic 3':5'-monophosphate (cAMP) in respiratory smooth muscle and inflammatory cells, respectively. Agents that elevate smooth muscle cAMP concentrations induce rapid bronchodilation and inhibit the release of inflammatory mediators from activated leukocytes [see Hardman, in *Smooth Muscle, An Assessment of Current Knowledge*, Univ. of Texas Press, (1981); and Nielson et al., *American Review of Respiratory Disease*, 137, 25 (1988)]. By virtue of their dual mechanisms of action, these compounds are expected to be highly effective as anti-asthmatic drugs.

Cyclic AMP concentrations within the living cell are determined by both the rate of its synthesis by adenylate cyclase and the rate of its degradation by phosphodiesterases (PDEs). Thus, either stimulating adenylate cyclase or inhibiting PDEs in pulmonary tissues can result in anti-asthmatic activities. This invention relates to compounds that inhibit a specific PDE, often called PDE IV, which selectively metabolizes cAMP and which is insensitive to the modulatory effects of guanosine cyclic 3':5' monophosphate (cGMP) and calcium. This PDE is found in both respiratory smooth muscle and inflammatory cells, and has been demonstrated to be a principal regulator of cAMP in these tissues [see Torphy and Cieslinski, *Molecular Pharmacology*, 37, 206 (1990), and Dent et al., *British Journal of Pharmacology*, 90, 163P (1990)]. Consequently, the compounds of the invention are bronchodilatory and antiinflamatory, and exhibit activity in animal models of allergic and nonallergic asthma. However, because the compounds of the invention have not been found to inhibit other forms of PDE, they are deemed to be more selective and safer anti-asthmatics than nonselective PDE inhibitors currently used for the treatment of asthma, such as theophylline.

The invention provides novel compounds of the formula

[structure: RO, CH₃O substituted phenyl with C∼R¹ and N—O—C(=O)—R²]

wherein
R is

[structure with (CH₂)ₐ, (CH₂)_b, (CH₂)_c bicyclic]

$C_{3-7}$alkyl, $C_{3-7}$cycloalkyl, (CH₂)ₐ (CH₂)_b,

[structure: R³-phenyl-(CH₂)ₘ—X—C(R⁴)(R⁵)—Y—(CH₂)ₙ—]

[structure: naphthyl-CH₂— or quinolinyl-CH₂—];

R¹ is hydrogen, lower alkyl or

[structure: R³-phenyl-Z—(CH₂)ₒ—];

a is 1–3;
b is 1–3;
c is 0–2;
X, Y and Z are each, independently, a bond, O, S or NH, with the proviso that if one of X or Y is O, S or NH, the other must be a bond;
R² is amino, loweralkylamino, arylamino, loweralkoxy or aryloxy;
R³ is hydrogen, halo, hydroxy, lower alkoxy, aryloxy, loweralkanoyloxy, amino, lower alkylamino, arylamino or loweralkanoylamino;
R⁴ and R⁵ are each, independently hydrogen or lower alkyl;
m is 0–4;
n is 1–4; and
o is 1–4.

The terms "lower alkyl", "lower alkoxy" and "lower alkanoyl" refer to moieties having 1 to 6 carbon atoms in the carbon chain. The term "aryl" refers to aromatic moieties having 6–10 carbon atoms. The term "halo" refers to fluoro, chloro and bromo.

The especially preferred compounds are those having the formula

[structure: RO, CH₃O substituted phenyl with C∼R¹ and N—O—C(=O)—R²]

wherein
R is $(C_{3-7})$alkyl, $(C_{3-7})$cycloalkyl, [bicyclic structure].

-continued

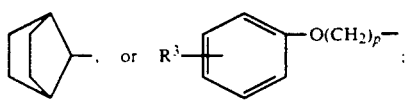

$R^1$ is hydrogen, lower alkyl or

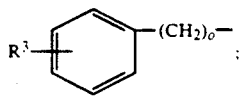

$R^2$ is amino, loweralkylamino, arylamino, loweralkoxy or aryloxy;

$R^3$ is hydrogen, halo, hydroxy, acetoxy, amino or acetamido;

o is 1–4; and p is 2–4.

The most preferred compounds are those in which $R^2$ is amino.

The compounds of the invention can be prepared by a basic reaction sequence, in which in the initial step isovanillin is reacted with a suitable R group-containing derivative, to yield an isovanillin intermediate with the appropriately substituted hydroxy group:

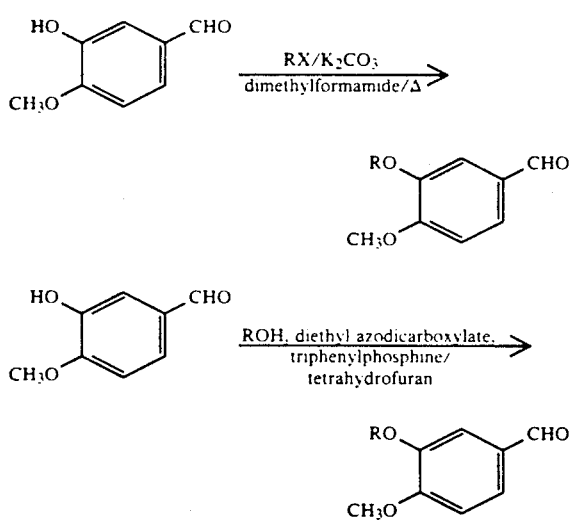

The latter is then reacted with an $R^1$ lithium derivative or appropriate Grignard reagent, followed by oxidation with pyridinium dichromate or $MnO_2$ to yield an appropriate ketone derivative

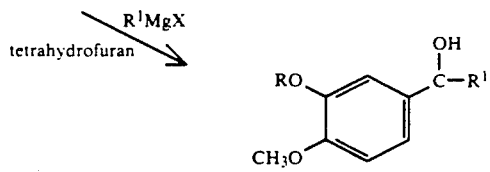

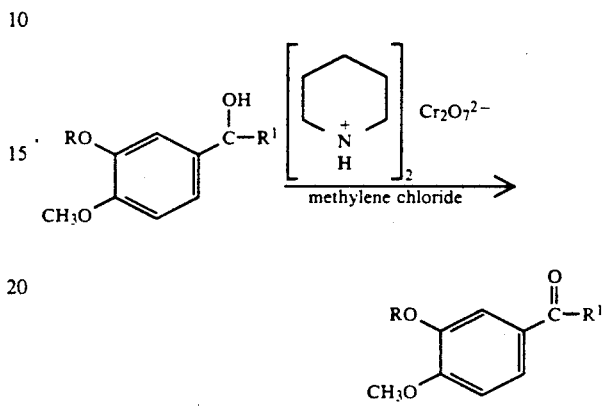

The ketone is then reacted with hydroxylamine hydrochloride, to yield the corresponding ketone oxime.

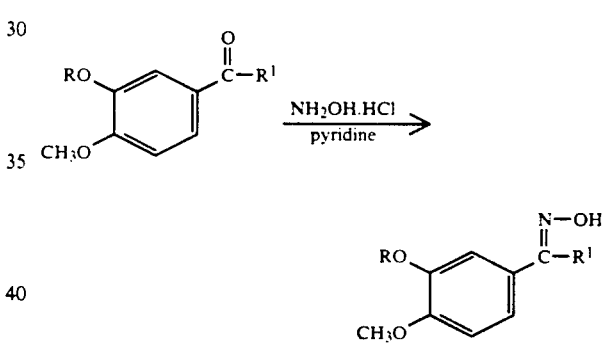

This ketone oxime is then reacted with appropriate reactants to yield the desired final product oxime carbamates or oxime carbonates. Thus, in order to prepare the N-unsubstituted oxime carbamates, an intermediate ketone oxime can be reacted with 1) chlorosulfonyl isocyanate in dry tetrahydrofuran, or with 2) trichloroacetyl isocyanate in dry tetrahydrofuran followed by reacting with ammonia, or with 3) sodium cyanate and trifluoroacetic acid in methylene chloride, or with 4) sodium cyanate and acetic acid and water:

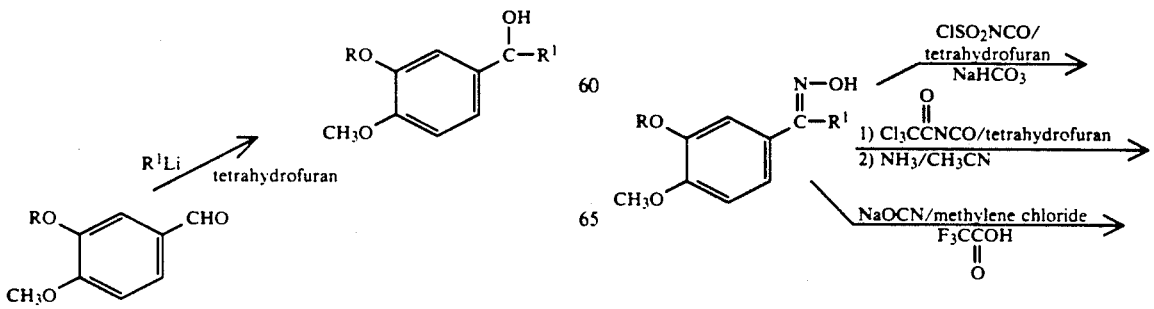

-continued

In like manner, N-substituted carbamates can be prepared by using an appropriately substituted alkyl or aryl isocyanate in dry tetrahydrofuran:

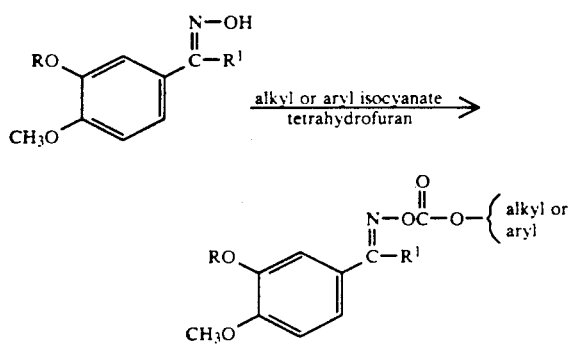

Finally, the oxime carbonates can be prepared by reacting the intermediate ketone oxime with an appropriate alkyl or aryl chloroformate in pyridine and methylene chloride:

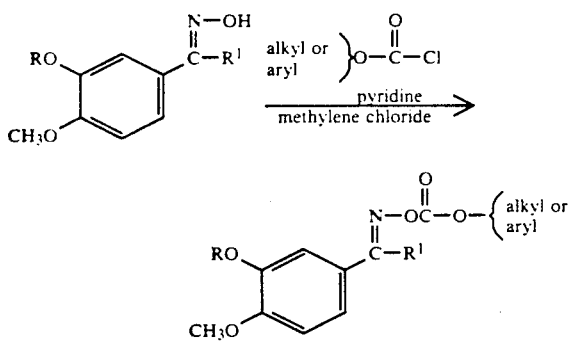

Of course, other methods of preparation, which will occur to those skilled in the art, may also be employed to prepare the compounds of this invention.

The starting materials used in the above-described preparative routes are commercially available, or can be made according to procedures taught in the chemical literature.

By virtue of possessing a double bond, the compounds of the invention possess cis-trans isomerism and hence the compounds of the invention embrace not only geometrical isomer mixtures, but the individual isomers as well. The isomers are designated according to the E/Z-system using the sequence rule.

The compounds of the invention, by virtue of their ability to inhibit PDE IV, are bronchodilatory and antiinflammatory, and are useful in the treatment of acute and chronic bronchial asthma and its associated pathology.

When the compounds of the invention are employed in the treatment of acute or chronic bronchial asthma, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may also be injected parenterally, in which case they are used in the form of a sterile solution containing other solutes, for example, enough saline or glucose to make the solution isotonic. For administration by inhalation or insufflation, the compounds may be formulated into an aqueous or partially aqueous solution, which can then be utilized in the form of an aerosol.

The dosage requirements vary with the particular compositions employed, the route of administration, the severity of the symptoms presented and the particular subject being treated. Treatment will generally be initiated with small dosages, less than the optimum dose of the compound. Thereafter the dosage is increased until the optimum effect under the circumstances is reached. In general, the compounds of the invention are most desirably administered at a concentration that will generally afford effective results without causing any harmful or deleterious side effects, and can be administered either as a single dose, or if desired, the dosage may be divided into convenient subunits administered at suitable times throughout the day.

The PDE IV inhibitory effects of the compounds of the invention may be demonstrated by standard pharmacological procedures, which are described more fully in the examples given hereinafter.

These procedures illustrate the ability of the compounds of the invention to inhibit PDE IV isolated from canine trachea.

The following examples show the preparation and pharmacological testing of compounds within the invention.

EXAMPLE 1

1-[3-(Cyclopentyloxy)-4-methoxyphenyl]ethanone (E)-O-(aminocarbonyl)oxime

A) 3-Cyclopentyloxy-4-methoxybenzaldeyde

To a magnetically-stirred solution of isovanillin (0.557 mol, 85.0 g) in dry dimethylformamide (500 mL) at room temperature was added powdered $K_2CO_3$ (0.558 mol, 77.1 g) in one portion followed by dropwise addition of neat cyclopentyl bromide (0.614 mol, 91.5 g; 65.9 mL). The resulting suspension is warmed to 60° C. and the reaction monitored by TLC until complete. Upon completion, the reaction mixture is cooled to room temperature and the dimethylformamide removed in vacuo. The residue is partitioned between water and ethyl acetate, the aqueous phase extracted with ethyl acetate and the combined organic layers are washed with water. The organics are dried ($Na_2SO_4$) and concentrated in vacuo to afford the alkylated product (0.317 mmol, 70.1 g; 57%) as a viscous oil which is of sufficient purity to be used as such in subsequent transformation.

NMR (DMSO-$d_6$, 300 MHz): δ 9.83 (s, 1H), 7.52 (dd, J=8.5; 2.0 Hz, 1H), 7.36 (d, J=2.0 Hz, 1H), 7.16 (d, J=8.5 Hz, 1H), 4.84 (m 1H), 3.83 (s, 3H), 1.70 (m, 8H).

B) α-Methyl-3-cyclopentyloxy-4-methoxybenzyl alcohol

To a magnetically-stirred solution of 3-cyclopentyloxy-4-methoxybenzaldehyde (59.0 mmol, 13.0 g) in dry tetrahydrofuran (500 mL) at −78° C. is added methyllithium (100 mmol, 90.0 mL; 1.4M solution in ethyl ether) dropwise over 30 minutes. The resulting solution is stirred at −78° C. for 30 minutes and quenched at −78° C. by the rapid addition of aqueous saturated NH$_4$Cl (140 mL). After warming to room temperature, water is added to dissolve the solids and the tetrahydrofuran was removed in vacuo. The residue is partitioned between water (500 mL) and ethyl acetate (500 mL), the aqueous phase extracted with ethyl acetate (500 mL) and the combined organic layers are washed with water (500 mL). The organics are dried (Na$_2$SO$_4$) and concentrated in vacuo to afford the title compound as a light yellow oil (58.3 mmol, 13.7 g; 99%). This material is of sufficient purity by TLC and NMR to be used as such in the subsequent transformation.

NMR (DMSO-d$_6$, 300 MHz) δ 6.91 (d, 1H), 6.84 (m, 2H), 5.00 (d, 1H), 4.76 (m, 1H), 3.70 (s, 3H), 1.70 (m, 8H), 1.27 (d, 3H).

C) 3-Cyclopentyloxy-4-methoxyacetophenone

To a magnetically-stirred solution of α-methyl-3-cyclopentyloxy-4-methoxybenzyl alcohol (58.3 mmol, 13.7 g) in dry methylene chloride (400 mL) at room temperature is added pyridinium dichromate (87.3 mmol, 32.8 g) in one portion. The resulting heterogeneous solution is stirred at room temperature overnight after which TLC indicated complete conversion to a faster running, UV-active spot. The reaction mixture is diluted with an equal volume of ethyl ether and stirred for 1 hr. The mixture is filtered through Celite and the filter cake was washed with ethyl ether (300 mL) and ethyl acetate (300 mL). The brown filtrate is concentrated in vacuo and purified by filtration through a plug of silica gel (methylene chloride eluent). The organics are removed in vacuo to afford the title compound as a light yellow solid (58.3 mmol, 13.6 g; 100%).

NMR (DMSO-d$_6$, 300 MHz) δ 7.59 (dd, J=8.5 Hz; 2.0 Hz, 1H), 7.40 (d, J=2.0 Hz, 1H), 7.03 (d, J=8.5 Hz, 1H), 4.82 (m, 1H), 3.80 (s, 3H), 2.50 (s, 3H), 1.70 (m, 8H).

D) 3-Cyclopentyloxy-4-methoxyacetophenone oxime

To a magnetically-stirred solution of 3-cyclopentyloxy-4-methoxyacetophenone (58.3 mmol, 13.6 g) in dry pyridine (300 mL) at room temperature is added hydroxylamine hydrochloride (64.0 mmol, 4.45 g) in one portion. The resulting suspension slowly becomes homogeneous, and the solution is stirred at room temperature overnight. The pyridine is removed in vacuo and the residue is partitioned between ethyl acetate (500 mL) and water (500 mL). The aqueous phase is extracted with water (400 mL). The organics are dried (Na$_2$SO$_4$) and concentrated in vacuo to afford the title compound as a tan solid (56.5 mmol, 14.1 g; 97%). This material is of sufficient purity by TLC and NMR to be used as such in the subsequent transformation without purification.

NMR (DMSO-d$_6$, 300 MHz) δ 11.0 (s, 1H), 7.24 (d, J=2.0 Hz, 1H), 7.13 (dd, J=8.5; 2.0 Hz, 1H), 6.94 (d, J=8.5 Hz, 1H), 4.77 (m, 1H), 3.75 (s, 3H), 2.10 (s, 3H), 1.80 (m, 8H)

E) 1-[3-(Cyclopentyloxy)-4-methoxyphenyl]ethanone (E)-O-(aminocarbonyl)oxime To a slowly-stirred suspension of NaOCN (160 mmol, 10.4 g.) in methylene chloride (30 mL) was added anhydrous trifluoroacetic acid (80.0 mmol, 9.12 g.; 6.16 mL) dropwise over 10 minutes at room temperature and the reaction vessel is loosely capped with a plastic stopper. The suspension slowly thickened to a gelatinous mass which is periodically agitated gently by hand. After 2 hours at room temperature, 3-cyclopentyloxy-4-methoxyacetophenone oxime (20.0 mmol, 4.98 g.) in methylene chloride (5 mL) is added in one portion and the reaction vessel is again stoppered. The reaction mixture is periodically agitated manually for 30 min. and then poured into saturated NaHCO$_3$ (250 mL) and extracted with methylene chloride (2×200 mL). The organic phase is washed with water (200 mL), dried (Na$_2$SO$_4$) and concentrated in vacuo to give a colorless oil. The oil was purified by flash chromatography (SiO$_2$: 1) 2.5% ethyl acetate/methylene chloride, 2) 5% ethyl acetate/methylene chloride), triturated with ethyl ether/hexane and dried in vacuo at 50° C. to afford analytically-pure title compound as a white solid (11.5 mmol, 3.37 g.; 58%).

NMR (DMSO-d$_6$, 300 MHz) δ 7.39 (d, J=2.0 Hz, 1H), 7.35 (dd, J=8.5; 2.0 Hz, 1H), 7.08 (br s, 2H), 6.85 (d, J=2.0 Hz, 1H), 4.92 (m, 1H), 3.78 (s, 3H), 2.29 (s, 3H), 1.71 (m, 8H).

IR (KBr) (cm$^{-1}$) 3460, 3250, 2960, 1715, 1600, 1522, 1375, 1265, 1225, 1143, 993, 978.

MS (EI, m/e (%)) 292 (M$^+$, 10), 249 (18), 181 (100), 164 (20), 124 (20).

Analysis for: C$_{15}$H$_{20}$N$_2$O$_4$; Calculated: C, 61.63; H, 6.90; N, 9.58. Found: C, 61.66; H, 7.06; N, 9.60.

An alternative procedure to step E) is the following:

1-[3-(Cyclopentyloxy)-4-methoxyphenyl]ethanone (E)-O-(aminocarbonyl)oxime

To a magnetically-stirred solution of 3-cyclopentyloxy-4-methoxyacetophenone oxime (23.4 mmol, 5.83 g.) in dry tetrahydrofuran (200 mL) at 0° C. is added chlorosulfonyl isocyanate (35.1 mmol, 4.97 g.; 3.06 mL) dropwise over 5 minutes. The resulting yellow solution is stirred at 0° C. for 15 minutes, the tetrahydrofuran is removed in vacuo, and the residue is partitioned between ethyl acetate (200 mL) and water (200 mL). The aqueous phase is extracted with ethyl acetate (200 mL) and the combined organic layers are washed with water (200 mL) and aqueous saturated NaHCO$_3$ (200 mL). The organics are dried (Na$_2$SO$_4$) and concentrated in vacuo to give a dark oil. This material is purified by flash chromatography (SiO$_2$: 5% ethyl acetate/methylene chloride) to give a light yellow solid which is subsequently triturated with a minimum of ethyl ether in hexane and collected by suction to afford the title compound as a white solid. The solid is dried overnight in vacuo at 50° C. to provide analytically-pure material (13.6 mmol, 3.97 g.; 58%).

NMR (DMSO-d$_6$, 300 MHz) δ7.39 (d, J=2.0 Hz, 1H), 7.35 (dd, J=8.5, 2.0 Hz, 1H), 7.08 (br s, 2H), 6.85 (d, J=2.0, 1H), 4.92 (m, 1H), 3.78 (s, 3H), 2.29 (s, 3H), 1.71 (m,8H).

IR (KBr) (cm$^{-1}$) 3460, 3250, 2960, 1715, 1600, 1522, 1375, 1265, 1225, 1143, 993, 978.

MS (EI, m/e (%)) 292 (M$^+$, 16), 224 (18), 182 (78), 180 (100), 164 (35), 140 (20), 124 (26).

Analysis for: $C_{15}H_{20}N_2O_4$: Calculated: C, 61.63; H, 6.90; N, 9.58. Found: C, 61.50; H, 6.88; N, 9.54.

EXAMPLE 2

1-[3-(Butoxy)-4-methoxyphenyl]ethanone (E)-O-(aminocarbonyl)oxime

A) 3-Butoxy-4-methoxybenzaldehyde

Following the procedure of Example 1A, from isovanillin (0.557 mol, 85.0 g), powdered $K_2CO_3$ (0.558 mol, 77.1 g), and n-butyl bromide (0.559 mol, 76.6 g; 60.0 mL) in dry dimethylformamide (500 mL) is obtained the alkylated product (0.557 mol, 118 g; 100%) as a white solid in sufficient purity to be used as such.

NMR (DMSO-$d_6$, 300 MHz): δ9.83 (s, 1H), 7.54 (dd, J=8.5; 2.0 Hz, 1H), 7.38 (d, J=2.0 Hz, 1H), 7.16 (d, J=8.5 Hz, 1H), 4.00 (t, 2H), 3.85 (s, 3H), 1.70 (m, 2H), 1.43 (m, 2H), 0.92 (t, 3H).

B) α-Methyl-3-butoxy-4-methoxybenzyl alcohol

Following the procedure of Example 1B, from 3-butoxy-4-methoxybenzaldehyde (24 mmol, 5.0 g) and methyllithium (26.4 mmol, 18.9 mL; 1.4M solution in ethyl ether) in dry tetrahydrofuran (150 mL) is obtained the alcohol (23.0 mmol, 5.15 g; 96%) which is shown to be about 93% pure by NMR. This material is used as such in the subsequent transformation without further purification.

NMR (CDCl$_3$, 300 MHz) δ6.94 (d, J=2.5 Hz, 1H), 6.85 (m, 2H), 4.82 (q, 1H), 4.01 (t, 2H), 3.85 (s, 3H), 1.82 (p, 2H), 1.50 (m, 3H), 0.97 (t, 2H).

C) 3-Butoxy-4-methoxyacetophenone

Following the procedure of Example 1C, from α-methyl-3-butoxy-4-methoxybenzyl alcohol (23 mmol, 5.15 g) and pyridinium dichromate (34.4 mmol, 12.95 g) in dry methylene chloride (150 mL) is obtained the ketone (21.6 mmol, 4.81 g; 94%) as a yellow solid of sufficient purity to be used as such without further purification.

NMR (CDCl$_3$, 300 MHz) δ7.52 (dd, J=8.5 Hz; 2.0 Hz, 1H), 7.51 (d, J=2.0 Hz, 1H), 6.86 (d, J=8.5 Hz, 1H), 4.05 (q, 2H), 3.90 (s, 3H), 2.55 (s, 3H), 1.83 (m, 2H), 1.48 (m, 2H), 0.95 (t, 3H).

D) 3-Butoxy-4-methoxyacetophenone oxime

Following the procedure of Example 1D, from 3-butoxy-4-methoxyacetophenone (15 mmol, 3.33 g) and hydroxylamine hydrochloride (16.5 mmol, 1.15 g) in dry pyridine (100 mL) is obtained the acetophenone oxime as a light yellow solid (13.17 mmol, 3.12 g; 88%) of sufficient purity to be used without further purification.

NMR (CDCl$_3$, 300 MHz) δ11.0 (s, 1H), 7.24 (d, J=2.0 Hz, 1H), 7.13 (dd, J=8.5; 2.0 Hz, 1H), 4.03 (t, J=7.0 Hz, 2H), 3.86 (s, 3H), 2.30 (s, 3H), 1.82 (m, 2H), 1.47 (m, 2H), 0.96 (t, J=7.0 Hz, 3H).

E) 1-[3-(Butoxy)-4-methoxyphenyl]ethanone (E)-O-(aminocarbonyl)oxime

Following the procedure of Example 1E, from 3-butoxy-4-methoxyacetophenone oxime (8.73 mmol, 1.94 g) and chlorosulfonyl isocyanate (4.63 mmol, 0.655 g; 0.403 mL) in dry tetrahydrofuran (40 mL) is obtained a yellow oil which is purified by flash chromatography (SiO$_2$: 1) methylene chloride, 2) 2% ethyl acetate/methylene chloride, 3) 5% ethyl acetate/methylene chloride). The residue was triturated with a minimum of ethyl ether in hexane and collected by suction to afford the title compound as a white solid. The solid was dried overnight in vacuo at 50° C. to provide analytically pure material (1.14 mmol, 0.306 g; 13%).

NMR (DMSO-$d_6$, 300 MHz) δ7.42 (d, J=2.0 Hz, 1H), 7.34 (dd, J=8.5, 2.0 Hz, 1H), 7.10 (s, 2H), 6.98 (d, J=8.5 Hz, 1H), 4.01 (t, 2H), 3.79 (s, 3H), 2.29 (s, 3H), 1.69 (m, 2H), 1.43 (m, 2H), 0.53 (t, 3H).

IR (KBr) (cm$^{-1}$) 3445, 3250, 2970, 1734, 1605, 1517, 1370, 1257, 1156, 1023, 975.

MS (EI, m/e (%)) 280 (14, M$^+$), 237 (100), 181 (99), 164 (65), 150 (48), 125 (37), 124 (94), 79 (30).

Analysis for: $C_{14}H_{20}N_2O_4$: Calculated: C, 59.99; H, 7.19; N, 9.99. Found: C, 59.97; H, 7.10; N, 9.87.

EXAMPLE 3

1-[4-Methoxy-3-(3-phenoxypropoxy)phenyl]ethanone (E)-O-(aminocarbonyl)oxime

A) 4-Methoxy-3-(3-phenoxypropoxy)-benzaldehyde

Following the procedure of Example 1A, from isovanillin (20 mmol, 3.04 g), powdered $K_2CO_3$ (22 mmol, 3.04 g), and 3-phenoxypropylbromide (22 mmol, 4.73 g; 3.47 mL) in dry dimethylformamide (100 mL) is obtained the alkylated product (20.0 mmol, 5.75 g; 100%) as a tan solid of sufficient purity to be used as such.

NMR (DMSO-$d_6$, 300 MHz): δ9.84 (s, 1H), 7.56 (dd, J=8.5; 2.0 Hz, 1H), d 7.44 (d, J=2.0 Hz, 1H), 7.28 (m, 2H), 7.18 (d, J=8.5 Hz, 1H), 6.94 (m, 3H), 4.20 (t, J=7.0 Hz, 2H), 4.13 (t, J=7.0 Hz, 2H), 3.66 (s, 3H), 2.20 (m, 2H).

B) α-Methyl-4-methoxy-3-(3-phenoxypropoxy)-benzyl alcohol

Following the procedure of Example 1B, from 4-methoxy-3-(3-phenoxypropoxy)benzaldehyde (8.03 mmol, 2.30 g) and methyllithium (12.05 mmol; 8.61 mL; 1.4M solution in ethyl ether) in dry tetrahydrofuran (100 mL) is obtained the title compound (7.57 mmol, 2.29 g; 94%) as a tan solid.

NMR (DMSO-$d_6$, 300 MHz) δ7.30 (m, 2H), 6.90 (m, 6H), 5.02 (d, 1H), 4.63 (m, 1H), 4.12 (t, J=7.0 Hz, 2H), 4.09 (t, J=7.0 Hz, 2H), 3.70 (s, 3H), 2.15 (p, 2H), 1.27 (d, 3H).

C) 4-Methoxy-3-(3-phenoxypropoxy)acetophenone

Following the procedure of Example 1C, from α-methyl-4-methoxy-3-(3-phenoxypropoxy)benzyl alcohol (7.51 mmol, 2.27 g) and pyridinium dichromate (11.26 mmol, 4.23 g) in dry methylene chloride (75 mL) is obtained the title compound (7.06 mmol, 2.12 g; 94%) as a light yellow solid of sufficient purity to be used directly in the subsequent transformation.

NMR (DMSO-$d_6$, 300 MHz) δ7.61 (dd, J=8.5; 2.0 Hz; 1H), 7.46 (d, J=8.5 Hz, 1H), 7.27 (m, 2H), 7.05 (d, 1H), 6.93 (m, 3H), 4.15 (t, J=7.0 Hz, 2H), 4.10 (t, J=7.0 Hz, 2H), 3.80 (s, 3H), 2.48 (s, 3H), 2.18 (m, 2H).

D) 4-Methoxy-3-(3-phenoxypropoxy)acetophenone oxime

Following the procedure of Example 1D, from 4-methoxy-3-(3-phenoxypropoxy)acetophenone (7.06 mmol, 2.12 g) and hydroxylamine hydrochloride (7.76 mmol, 540 mg) in dry pyridine (70 mL) is obtained the title compound as an off-white solid (6.60 mmol, 2.08 g; 93%) of sufficient purity to be used as such in the subsequent transformation.

NMR (DMSO-d$_6$, 300 MHz) δ10.95 (s, 1H), 7.25 (m, 3H), 7.16 (d, J=2.0 Hz, 1H), 6.93 (m, 4H), 4.12 (t, J=7.5 Hz, 2H), 4.09 (t, J=7.5 Hz, 2H), 3.77 (s, 3H), 2.15 (m, 2H), 2.10 (s, 3H).

E)

1-[4-Methoxy-3-(3-phenoxypropoxy)phenyl]ethanone (E)-O-(aminocarbonyl)oxime

Following the procedure of Example 1E, to a slowly-stirred suspension of sodium isocyanate (19.02 mmol, 1.24 g) in dry methylene chloride (20 mL) is added anhydrous trifluoroacetic acid (38.05 mmol, 4.34 g; 2.93 ml) and a solution of 4-methoxy-3-(3-phenoxypropoxy)acetophenone oxime (4.76 mmol, 1.50 g) in methylene chloride (6 mL) to obtain a yellow oil which is purified by flash chromatography (SiO$_2$: 1) 5% ethyl acetate/methylene chloride, 2) 8% ethyl acetate/methylene chloride, 3) 10% ethyl acetate/methylene chloride). The resulting white solid is dried in vacuo to afford analytically pure title compound (3.12 mmol, 1.12 g; 66%).

NMR (DMSO-d$_6$, 300 MHz) δ7.47 (d, J=2.0 Hz, 1H), 7.36 (dd, J=8.5; 2.0 Hz, 1H), 7.27 (m, 2H), 7.11 (s, 2H), 6.95 (m, 4H), 4.19 (t, J=7.0 Hz, 2H), 4.12 (t, J=7.0 Hz, 2H), 3.78 (s, 3H), 2.28 (s, 3H), 2.16 (t, 2H).

IR (KBr) (cm$^{-1}$) 3470, 3250, 2940, 1730, 1605, 1590, 1520, 1370, 1258, 1152, 975, 758.

MS (EI, m/e (%)) 358 (M$^-$, 0.6), 315 (55), 164 (23), 107 (100), 77 (75).

Analysis for: C$_{19}$H$_{22}$N$_2$O$_5$; Calculated: C, 63.67; H, 6.19; N, 7.82. Found: C, 64.01; H, 6.08; N, 7.71.

EXAMPLE 4

1-(3-Cyclopentyloxy-4-methoxyphenyl)-2-phenylethanone (E)-O-(aminocarbonyl)oxime A) 1-(3-Cyclopentyloxy-4-methoxyphenyl)-2-phenyl ethan-1-ol To a magnetically-stirred solution of freshly crushed magnesium turnings (36.54 mmol, 0.888 g) in anhydrous ethyl ether (20 mL) at room temperature is added a solution of benzyl bromide (36.54 mmol, 4.35 mL) in anhydrous ethyl ether (15 mL) dropwise via addition funnel. The addition is slow at first; only 2 to 3 mL of reagent is added and the reaction mixture is heated until gas evolution is observed. Dropwise addition of benzyl bromide is begun at this point, and the reaction mixture is diluted with ethyl ether (20 mL) to prevent dimerization of the Grignard reagent. Once the addition of benzyl bromide is complete, the reaction is allowed to stir at room temperature for 1 hour and then a solution of 3-cyclopentyloxy-4-methoxybenzaldehyde (30.00 mmol, 6.61 g) in anhydrous ethyl ether (30 mL) is added dropwise at room temperature. The reaction mixture is allowed to stir at room temperature for 30 minutes and then poured into a solution of ice water (500 mL) containing concentrated H$_2$SO$_4$ (7 mL). The aqueous mixture is extracted with ethyl acetate (2×300 mL) and the combined organic layers are washed with saturated NaHCO$_3$ (300 mL). The organic layer is dried (Na$_2$SO$_4$) and concentrated in vacuo to afford the title compound as a white solid (25.97 mmol, 8.06 g; 86%) of sufficient purity to be used directly in subsequent transformation.

B)

1-(3-Cyclopentyloxy-4-methoxyphenyl)-2-phenylethanone

Following the procedure of Example 1C, from 1-(3-cyclopentyloxy-4-methoxyphenyl)-2-phenylethan-1-ol (10.0 mmol, 3.12 g) and pyridinium dichromate (15.0 mmol, 5.64 g) in dry methylene chloride (100 mL) is obtained the ketone as a light yellow solid (9.05 mmol, 2.81 g; 90%) of sufficient purity to be used as such in subsequent transformation without purification.

NMR (CDCl$_3$, 300 MHz) δ7.63 (dd, J=8.5 Hz; 2.0 Hz, 1H), 7.54 (d, J=2.0 Hz, 1H), 7.28 (m, 5H), 6.86 (d, J=8.5 Hz, 1H), 4.80 (m, 1H), 4.22 (s, 2H), 3.89 (s, 3H), 1.80 (m, 8H).

C)

1-(3-Cyclopentyloxy-4-methoxyphenyl)-2-phenylethanone oxime

Following the procedure of Example 1D, from 1-(3-cyclopentyloxy-4-methoxyphenyl)-2-phenylethanone (5.0 mmol, 1.55 g) and hydroxyamine hydrochloride (5.50 mmol, 0.382 g) in dry pyridine (25 mL) is obtained the title compound as a yellow solid (4.61 mmol, 1.50 g, 93%) of sufficient purity to be used as such in the subsequent transformation.

NMR (DMSO-d$_6$, 300 MHz) δ11.27 (s, 1H), 7.20 (m, 7H), 6.89 (m, 8H), 4.70 (m, 1H), 4.12 (s, 2H), 3.70 (s, 3H), 1.65 (m, 8H).

D)

1-(3-Cyclopentyloxy-4-methoxyphenyl)-2-phenylethanone(E)-O-(aminocarbonyl)oxime

To a magnetically-stirred solution of 1-(3-cyclopentyloxy-4-methoxyphenyl)-2-phenyl ethanone oxime (4.51 mmol, 1.48 g) in dry tetrahydrofuran (45 mL) at 0° C. is added trichloroacetyl isocyanate (5.00 mmol, 0.943 mg; 0.596 mL) dropwise over 2 minutes and the resulting solution is allowed to stir as the temperature rises slowly from 0° C. to room temperature overnight. The reaction mixture is then cooled to 0° C. and saturated NH$_3$/acetonitrile solution (25 mL; prepared by bubbling gaseous ammonia through CH$_3$CN at room temperature for 1 hour) is added dropwise to the reaction mixture. The solution is allowed to stir as it warms slowly from 0° C. to room temperature. After 1.5 hours, the tetrahydrofuran is removed in vacuo and the residue is partitioned between methylene chloride (200 mL) and water (200 mL). The aqueous phase is extracted with ethyl acetate (200 mL) and the combined organics are washed with water (200 mL), dried (Na$_2$SO$_4$), and concentrated in vacuo to afford a mixture of product and oxime (~1:1). The residue is purified via flash chromatography (SiO$_2$: 1) 2% ethyl acetate/methylene chloride, 2) 5% ethyl acetate/methylene chloride, 3) 7% ethyl acetate/methylene chloride) to give a white solid which is triturated with ether/hexane and dried in vacuo at 50° C. to afford analytically-pure title compound (1.22 mmol, 0.450 g; 27%).

NMR (DMSO-d$_6$, 300 MHz) δ7.38 (m, 2H), 7.24 (m, 2H), 7.17 (m, 5H), 6.94 (d, J=8.5 Hz, 1H), 4.84 (m, 1H), 4.23 (s, 2H), 3.74 (s, 3H), 1.65 (m, 8H).

IR (KBr) (cm$^{-1}$) 3925, 3815, 3240, 2950, 2920, 1710, 1588, 1511, 1358, 1252, 1222, 1130, 960, 898.

MS (FAB, m/e (%)) 391 (22, M+Na$^+$), 368 (21, M$^+$), 310 (100), 308 (66), 91 (85).

Analysis for: C$_{21}$H$_{24}$N$_2$O$_4$; Calculated: C, 68.46; H, 6.57; N, 7.60. Found: C, 68.42; H, 6.71; N, 7.48.

EXAMPLE 5

1-(3-Cyclopentyloxy-4-methoxyphenyl)-3-phenyl-propanone (E)-O-(aminocarbonyl)oxime

A)

1-(3-Cyclopentyloxy-4-methoxyphenyl)-3-phenylpropan-1-ol

Following the procedure of Example 4A, from magnesium turnings (32.42 mmol, 0.788 g), 2-bromoethylbenzene (32.42 mmol, 6.00 g), 3-cyclopentyloxy-4-methoxybenzaldehyde (32.42 mmol, 7.14 g) of Example 1A, and anhydrous ethyl ether (300 mL) is obtained the title compound as a white solid (29.4 mmol, 9.60 g; 91%) which is of sufficient purity to be used directly without further purification.

NMR (DMSO-$d_6$, 300 MHz) δ7.21 (m, 5H), 6.89 (d, J=2.0 Hz, 1H), 6.87 (d, J=8.5 Hz, 1H), 6.80 (dd, J=8.5; 2.0 Hz, 1H), 5.12 (d, 1H), 4.76 (m, 1H), 4.42 (m, 1H), 3.70 (s, 3H), 2.58 (m, 2H), 2.73 (m, 10H).

B)

1-(3-Cyclopentyloxy-4-methoxyphenyl)-3-phenyl-propanone

Following the procedure of Example 1C, from 1-(3-cyclopentyloxy-4-methoxyphenyl)-3-phenylpropan-1-ol (29.41 mmol, 9.60 g) and pyridinium dichromate (44.12 mmol, 16.59 g) in dry methylene chloride (120 mL) is obtained the ketone as a light yellow solid which is shown by TLC to contain a small amount of 3-cyclopentyloxy-4-methoxybenzaldehyde. This material was partitioned between aqueous saturated $NaHSO_3$ (500 mL) and ethyl acetate (500 mL) to remove traces of aldehyde leftover from the Grignard reaction. The aqueous phase is washed with ethyl acetate (500 mL), and the organic layers are combined, dried ($Na_2SO_4$), and concentrated in vacuo to afford the title compound as a white solid (23.74 mmol, 7.70 g; 89%) in sufficient purity to be used as such without further purification.

NMR (DMSO-$d_6$, 300 MHz) δ7.64 (dd, J=8.5 Hz; 2.0 Hz, 1H), 7.43 (d, J=2.0 Hz, 1H), 7.28 (s, 2H), 7.26 (s, 2H), 7.18 (m, 1H), 7.04 (d, J=8.5 Hz, 1H), 4.82 (m, 1H), 3.80 (s, 3H), 3.30 (t, J=7.0 Hz, 2H), 2.90 (t, J=7.0 Hz, 2H), 1.70 (m, 8H).

C)

1-(3-Cyclopentyloxy-4-methoxyphenyl)-3-phenyl-propanone oxime

Following the procedure of Example 1D, from 1-(3-cyclopentyloxy-4-methoxyphenyl)-3-phenylpropanone (9.25 mmol, 3.00 g) and hydroxylamine hydrochloride (10.17 mmol, 0.707 g) in anhydrous pyridine (90 mL) is obtained the oxime as a light yellow solid (8.54 mmol, 2.90 g; 92%) which is sufficiently pure to be used as such without further purification.

NMR (DMSO-$d_6$, 300 MHz) δ11.07 (s, 1H), 7.22 (m, 7H), 6.94 (d, J=8.5 Hz, 1H), 4.75 (m, 1H), 3.75 (s, 3H), 2.94 (t, 2H), 2.73 (t, 2H), 1.70 (m, 8H).

D)

1-(3-Cyclopentyloxy-4-methoxyphenyl)-3-phenyl-propanone (E)-O-(aminocarbonyl)oxime Following the alternative procedure to Example 1E, from 1-(3-cyclopentyloxy-4-methoxyphenyl)-3-phenyl-propanone oxime (8.54 mmol, 2.90 g) and chlorosulfonyl isocyanate (12.82 mmol, 1.81 g; 1.12 mL) in dry tetrahydrofuran (80 mL) is obtained a yellow oil which is purified by flash chromatography ($SiO_2$: 1) methylene chloride, 2) 2% ethyl acetate/methylene chloride, 3) 5% ethyl acetate/methylene chloride, 4) 10% ethyl acetate/methylene chloride). The residue is triturated with a minimum of ethyl ether in hexane and collected by suction to afford the title compound as a white solid. The solid is dried overnight in vacuo at 50° C. to provide analytically-pure material (2.53 mmol, 0.969 g; 30%).

NMR (DMSO-$d_6$, 300 MHz) δ7.26 (m, 7H), 7.07 (s, 2H), 6.99 (d, J=2.0 Hz, 1H), 4.86 (m, 1H), 3.78 (s, 3H), 3.07 (t, 2H), 2.78 (t, 2H), 1.7 (m, 8H).

IR (KBr) ($cm^{-1}$) 3480, 3310, 3260, 2940, 1710, 1550, 1515, 1357, 1266, 1218, 1125, 1015, 975, 695.

MS (EI, m/e) 382 (0.5, $M^+$), 339 (24), 254 (60), 213 (22), 150 (100), 149 (31), 105 (20), 91 (50).

Analysis for: $C_{22}H_{26}N_2O_4$; Calculated: C, 69.09; H, 6.85; N, 7.33. Found: C, 68.81; H, 6.82; N, 7.04.

EXAMPLE 6

1-[3-(Cyclopentyloxy)-4-methoxyphenyl]-3-methyl-butanone (E)-O-(aminocarbonyl)oxime

A)

1-(3-Cyclopentyloxy-4-methoxyphenyl)-3-methylbutan-1-ol

To a magnetically-stirred solution of 3-cyclopentyloxy-4-methoxybenzaldehyde (25.0 mmol, 5.50 g) of Example 1A, in anhydrous ethyl ether (250 mL) at 0° C. is added isobutylmagnesium chloride (30 mmol, 15 mL; 2.0M solution in ethyl ether) dropwise over 20 minutes. The reaction mixture is allowed to stir while slowly warming to room temperature over 1 hour and is then poured into 1N HCl (250 mL) and partitioned with ethyl ether (200 mL). The aqueous phase is extracted with ethyl ether (200 mL) and the combined organics are washed with aqueous saturated $NaHCO_3$ (200 mL), aqueous saturated NaCl (200 mL), and dried ($MgSO_4$). Concentration in vacuo affords a yellow oil which is purified by flash chromatography ($SiO_2$: 1) methylene chloride, 2) 2% ethyl acetate/methylene chloride, 3) 5% ethyl acetate/methylene chloride) to give the title compound as a white solid (21.5 mmol, 5.98 g; 86%).

NMR (DMSO-$d_6$, 300 MHz) δ6.82 (m, 3H), 4.93 (d, 1H), 4.76 (m, 1H), 4.43 (m, 1H), 3.68 (s, 3H), 1.60 (m, 8H), 1.30 (m, 2H), 0.85 (d, 6H).

B)

1-(3-Cyclopentyloxy-4-methoxyphenyl)-3-methylbutanone

Following the procedure of Example 1C, from 1-(3-cyclopentyloxy-4-methoxyphenyl)-3-methylbutan-1-ol (21.5 mmol, 5.98 g) and pyridinium dichromate (33.0 mmol, 12.4 g) in dry methylene chloride (125 mL) is obtained the ketone as a light yellow oil (21.0 mmol, 5.80 g; 98%) of sufficient purity to be used as such in subsequent transformation.

NMR (DMSO-$d_6$, 300 MHz) δ7.56 (dd, J=8.5; 2.0 Hz, 1H), 7.53 (d, J=2.0 Hz, 1H), 6.87 (d, J=8.5 Hz, 1H), 4.85 (m, 1H), 3.93 (s, 3H), 2.79 (d, 2H), 2.30 (m, 1H), 1.80 (m, 8H), 1.00 (d, 6H).

C)

1-(3-Cyclopentyloxy-4-methoxyphenyl)-3-methylbutanone oxime

Following the procedure of Example 1D, from 1-(3-cyclopentyloxy-4-methoxyphenyl)-3-methylbutanone (10.0 mmol, 2.76 g) and hydroxyamine hydrochloride (11.0 mmol, 0.765 g) in dry pyridine (50 mL) is obtained the title compound as a colorless oil which solidifies on standing (9.51 mmol, 2.77 g, 95%). This material is of sufficient purity to be used as such in the subsequent transformation.

NMR (DMSO-d$_6$, 300 MHz) δ10.92 (s, 1H), 7.20 (d, J=2.0 Hz, 1H), 7.13 (dd, J=8.5; 2.0 Hz, 1H), 6.94 (d, J=8.5 Hz, 1H), 4.78 (m, 1H), 3.73 (s, 3H), 2.60 (d, 2H), 1.70 (m, 8H), 0.84 (d, 6H).

D)
1-[3-(Cyclopentyloxy)-4-methoxyphenyl]-3-methyl-butanone (E)-O-(aminocarbonyl)oxime Following the procedure of Example 1E, to a slowly stirred suspension of sodium isocyanate (32.0 mmol, 2.08 g) in dry methylene chloride (30 mL) is added anhydrous trifluoroacetic acid (16.0 mmol, 1.82 g; 1.23 mL) and a solution of 1-(3-cyclopentyloxy-4-methoxyphenyl)-3-methylbutanone oxime (4.0 mmol, 1.16 g) in methylene chloride (10 mL) to afford a yellow oil which is purified by flash chromatography (SiO$_2$: 1) methylene chloride, 2) 1% ethyl acetate/methylene chloride, 3) 3% ethyl acetate/methylene chloride, 4) 6% ethyl acetate/methylene chloride). The residue is triturated overnight with ethyl ether/hexane and dried in vacuo at 50° C. to afford analytically pure title compound as a white solid (2.40 mmol, 0.802 g; 60%).

NMR (DMSO-d$_6$, 300 MHz) δ7.35 (m, 2H), 7.05 (s, 2H), 6.98 (m, 1H), 4.90 (m, 1H), 3.78 (s, 3H), 2.74 (d, 2H), 1.72 (m, 9H), 0.86 (d, 6H).

IR (KBr) (cm$^{-1}$) 3440, 3310, 3200, 2956, 2874, 1722, 1618, 1515, 1360, 1260, 990.

MS (EI, m/e (%)) 334 (M$^+$, 4), 291 (11), 223 (13), 206 (100), 165 (52), 150 (65), 149 (66).

Analysis for: C$_{18}$H$_{26}$N$_2$O$_4$; Calculated: C, 64.64; H, 7.84; N, 8.38. Found: C, 64.97; H, 7.85; N, 8.36.

EXAMPLE 7
1-[3-(Cyclopentyloxy)-4-methoxyphenyl]ethanone (E)-O-[(methylamino)carbonyl]oxime To a magnetically-stirred solution of 3-cyclopentyloxy-4-methoxyacetophenone oxime (2.0 mmol, 0.5 g) of Example 1D, in dry tetrahydrofuran (20 mL) at 0° C. is added methyl isocyanate (2.20 mmol, 0.126 g; 0.126 g; 0.130 mL) dropwise over 1 minute followed by a catalytic amount of 4-dimethylaminopyridine (4-DMAP). The reaction mixture is allowed to stir while warming slowly from 0° C. to room temperature over 4 hours while being monitored by TLC. After 4 hours, another equivalent of methyl isocyanate (0.130 mL) is added at room temperature and the reaction is allowed to stir overnight. The tetrahydrofuran is removed in vacuo and the residue is partitioned between methylene chloride (100 mL) and water (100 mL). The aqueous phase is extracted with methylene chloride (100 mL) and the combined organics are washed with water (100 mL), dried (Na$_2$SO$_4$), and concentrated in vacuo. The residue is purified by flash chromatography (SiO$_2$: 1) methylene chloride, 2) 2% ethyl acetate/methylene chloride, 3) 5% ethyl acetate/methylene chloride) and triturated with hexane to give title compound as a white solid which is dried overnight in vacuo at 50° C. to provide analytically-pure material (1.58 mmol, 0.493 g; 80%).

NMR (DMSO-d$_6$, 300 MHz) δ7.39 (dd, J=8.5, 2.0 Hz, 1H), 7.37 (d, J=2.0 Hz, 1H), 6.99 (d, J=8.5 Hz, 1H), 4.90 (m, 1H), 3.77 (s, 3H), 2.70 (d, 2H), 2.29 (s, 3H), 1.70 (m, 8H).

IR (KBr) (cm$^{-1}$) 3575, 3408, 2960, 1714, 1500, 1427, 1280, 1253, 1233, 1150, 958.

MS (EI, m/e (%)) 306 (20, M$^+$), 249 (9), 216 (19), 185 (19), 181 (100), 164 (20), 86 (43), 84 (65).

Analysis for: C$_{16}$H$_{22}$N$_2$O$_4$; Calculated: C, 62.73; H, 7.24; N, 9.14. Found: C, 62.60; H, 7.28; N, 9.15.

EXAMPLE 8
1-(3-butoxy-4-methoxyphenyl)ethanone (E)-O-[(methylamino)carbonyl]oxime Following the procedure of Example 7, from 3-butoxy-4-methoxyacetophenone oxime (2.10 mmol, 0.498 g) of Example 2D, and methyl isocyanate (3.46 mmol, 0.198 g; 0.204 mL) in dry tetrahydrofuran (20 mL) containing a catalytic amount of 4-dimethylaminopyridine is obtained a yellow oil which is purified by flash chromatography (SiO$_2$: 1) methylene chloride, 2) 2% ethyl acetate/methylene chloride). Trituration with hexane and collection via suction affords title compounds as a white solid which is dried overnight in vacuo at 50° C. to provide analytically-pure material. (1.46 mmol, 0.430 g; 70%)

NMR (DMSO-d$_6$, 300 MHz) δ7.40 (m, 3H), 6.99 (d, J=8.5 Hz, 1H), 4.01 (t, 2H), 3.79 (s, 3H), 2.70 (d, J=3.5 Hz, 2H), 2.30 (s, 3H), 1.69 (m, 2H), 1.42 (m, 2H), 0.93 (t, 3H).

IR (KBr) (cm$^{-1}$) 3355, 2970, 2950, 2883, 1717, 1520, 1464, 1332, 1266, 1234, 1152, 1033, 960.

MS (EI, m/e (%)) 294 (31, M$^+$), 150 (56), 149 (30), 148 (23), 237 (100), 181 (79), 180 (30), 165 (40), 164 (48), 140 (42), 135 (29), 125 (30), 124 (56), 79 (34).

Analysis for: C$_{15}$H$_{22}$N$_2$O; Calculated: C, 61.21; H, 7.53; N, 9.52. Found: C, 60.58; H, 7.56; N, 9.41.

EXAMPLE 9
1-(3-butoxy-4-methoxyphenyl)ethanone (E)-O-[(phenylamino)carbonyl]oxime Following the procedure of Example 7, from 3-butoxy-4-methoxyacetophenone oxime (1.50 mmol, 0.356 g) of Example 2D, and phenyl isocyanate (1.65 mmol, 0.196 g, 0.179 mL) in dry tetrahydrofuran (15 mL) containing a catalytic amount of 4-dimethylaminopyridine is obtained a yellow oil which is purified by flash chromatography (SiO$_2$: 1) 2:1 methylene chloride/hexane, 2) methylene chloride). Trituration with hexane affords a white solid which is collected by suction and dried in vacuo overnight at 50° C. to provide analytically-pure title compound (0.97 mmol, 0.347 g; 65%).

NMR (DMSO-d$_6$, 300 MHz) δ9.78 (s, 1H), 7.53 (dd, J=8.5; 2.0 Hz, 2H), 7.34 (m, 4H), 7.04 (m, 2H), 4.00 (t, 2H), 3.81 (s, 3H), 2.48 (s, 3H), 1.70 (m, 2H), 1.44 (m, 2H), 0.93 (t, 3H).

IR (KBr) (cm$^{-1}$) 3270, 3140, 3080, 2985, 2965, 1734, 1600, 1552, 1517, 1444, 1320, 1250, 1230, 1210, 1165, 1015, 765.

MS (FAB, m/e (%)) 356 (20, M$^+$), 328 (7), 312 (21), 222 (52), 220 (100), 164 (5), 123 (8).

Analysis for: C$_{20}$H$_{24}$N$_2$O$_4$; Calculated: C, 67.40; H, 6.79; N, 7.86. Found: C, 67.53; H, 6.59; N, 7.96.

EXAMPLE 10
1-[3-(cyclopentyloxy)-4-methoxyphenyl]ethanone (E)-O-(methoxycarbonyl)oxime To a magnetically-stirred solution of 3-cyclopentyloxy-4-methoxyacetophenone oxime (1.90 mmol, 0.474 g) of Example 1D, in dry methylene chloride (20 mL) at 0° C. is added pyridine (3.42 mmol, 0.271 g; 0.277 mL) followed by the dropwise addition of methyl chloroformate (2.28 mmol, 0.215 g; 0.176 mL). The resulting yellow solution is stirred while warming slowly to room temperature over 5 hours. The reaction mixture is diluted with methylene chloride (100 mL) and partitioned with water (100 mL). The aqueous phase is extracted with methylene chloride (100 mL) and the combined organic layers are washed with water (100 mL). The organics are dried ($Na_2SO_4$) and concentrated in vacuo to give a yellow solid which is subsequently triturated with a minimum of ethyl ether in hexane and collected by suction to afford the title compound as a white solid. The solid is dried overnight in vacuo at 50° C. to provide analytically-pure material (1.19 mmol, 0.365 g; 62.5%).

NMR (DMSO-$d_6$, 300 MHz) δ7.30 (dd, J=8.5, 2.0 Hz, 1H), 7.28 (d, J=2.0 Hz, 1H), 7.02 (d, J=8.5 Hz, 1H), 4.80 (m, 1H), 3.81 (s, 3H), 3.78 (s, 3H), 2.30 (s, 3H), 1.70 (m, 8H).

IR (KBr) ($cm^{-1}$) 2970, 1790, 1580, 1510, 1540, 1525, 1248, 1150, 1020, 988, 844, 778.

MS (EI, m/e (%)) 307 (27, $M^-$), 239 (54), 165 (35), 164 (81), 148 (100), 123 (32), 122 (55).

Analysis for: $C_{16}H_{21}NO_5$; Calculated: C, 62.52; H, 6.89; N, 4.56. Found: C, 62.49; H, 6.72; N, 4.49.

EXAMPLE 11

1-(3-butoxy-4-methoxyphenyl)ethanone (E)-O-(methoxycarbonyl)oxime

Following the procedure of Example 10, from 3-butoxy-4-methoxyacetophenone oxime (1.80 mmol, 0.427 g) of Example 2D, pyridine (2.0 mmol, 0.158 g; 0.162 mL), and methyl chloroformate (2.0 mmol, 0.189 g; 0.154 mL) in dry methylene chloride (20 mL) is obtained an off-white solid which is purified by flash chromatography ($SiO_2$: 1) 2:1 methylene chloride/hexane, 2) 4:1 methylene chloride/hexane, 3) methylene chloride). The resulting material is dried overnight in vacuo at 50° C. to provide analytically-pure title compound as a white solid (1.59 mmol, 0.470 g; 88%).

NMR (DMSO-$d_6$, 300 MHz) δ7.30 (dd, J=8.5, 2.0 Hz, 1H), 7.28 (d, J=2.0 Hz, 1H), 7.02 (d, J=8.5 Hz, 1H), 3.87 (t, 2H), 3.81 (s, 3H), 3.80 (s, 3H), 2.31 (s, 3H), 1.70 (m, 2H), 1.44 (m, 2H), 0.93 (m, 3H).

IR (KBr) ($cm^{-1}$) 3400, 2970, 2950, 1785, 1520, 1442, 1430, 1317, 1245, 1152, 1020, 938, 878, 783.

MS (EI, m/e (%)) 295 (51, $M^+$), 220 (26), 164 (64), 149 (33), 148 (100), 134 (34), 123 (37), 122 (54), 79 (34).

Analysis for: $C_{15}H_{21}NO_5$; Calculated: C, 61.00; H, 7.17; N, 4.74. Found: C, 60.99; H, 7.23; N, 4.76.

EXAMPLE 12

1-(3-butoxy-4-methoxyphenyl)ethanone (E)-O-(phenoxycarbonyl)oxime

Following the procedure of Example 10, from 3-butoxy-4-methoxyacetophenone oxime (1.50 mmol, 0.356 g) of Example 2D, pyridine (1.65 mmol, 0.130 g; 0.133 mL), and phenyl chloroformate (1.65 mmol, 0.258 g; 0.207 mL) in dry methylene chloride (15 mL) is obtained a yellow oil which is purified by flash chromatography ($SiO_2$: 1) 1:1 methylene chloride/hexane, 2) 2:1 methylene chloride/hexane). Subsequent trituration with a minimum of ethyl ether in hexane gives title compound as a white solid which is dried overnight in vacuo at 50° C. to provide analytically-pure material (0.42 mmol, 0.150 g; 28%).

NMR (DMSO-$d_6$, 300 MHz) δ7.47 (m, 2H), 7.33 (m, 5H), 7.05 (d, J=8.5 Hz, 1H), 3.98 (t, 2H), 3.81 (s, 3H), 2.40 (s, 3H), 1.70 (m, 2H), 1.43 (m, 2H), 0.93 (t, 3H).

IR (KBr) ($cm^{-1}$) 3440, 2960, 2930, 2850, 1790, 1600, 1523, 1330, 1260, 1220, 1180, 1140, 1020.

MS (EI, m/e (%)) 357 (9.1, $M^+$), 221 (24), 220 (100), 165 (19), 150 (17), 123 (18), 94 (19).

Analysis for: $C_{20}H_{23}NO_5$; Calculated: C, 67.21; H, 6.49; N, 3.92. Found: C, 65.35; H, 6.54; N, 3.77.

EXAMPLE 13

1-[3-(bicyclo[2.2.1]hept-2-yloxy)-4-methoxyphenyl]ethanone (E)-O-(aminocarbonyl)oxime

A)

3-(Bicyclo[2.2.1]hept-2-yloxy)-4-methoxybenzaldehyde

To a magnetically-stirred solution of isovanillin (10 mmol, 1.52 g) in dry tetrahydrofuran (15 mL) at −10° C. is added endo-norborneol (10 mmol, 1.12 g) followed by triphenylphosphine (14 mmol, 3.67 g). After a few minutes, a solution of diethylazodicarboxylate (14 mmol, 2.44 g; 2.22 mL) in dry tetrahydrofuran (5 mL) is added dropwise at −10° C. and the resulting solution is allowed to warm to room temperature over 20 hours. The solvent is removed in vacuo and the residue partitioned between ethyl acetate and water. The organic phase is dried ($Na_2SO_4$) and concentrated in vacuo to afford the crude product. This material is purified by flash chromatography ($SiO_2$: 20% ethyl acetate/hexane) to give the title compound as a colorless oil (4.07 mmol, 1.00 g; 41%).

NMR (DMSO-$d_6$, 300 MHz): δ9.82 (s, 1H), 7.55 (dd, J=8.5, 2.0 Hz, 1H), 7.30 (d, J=2.0 Hz, 1H), 7.18 (d, J=8.5 Hz, 1H), 4.30 (d, J=5.0 Hz, 1H), 3.85 (s, 3H), 2.38 (d, J=5.0 Hz, 1H), 2.29 (s, 1H), 1.80 (m, 1H), 1.48 (m, 4H), 1.16 (m, 3H).

B)

α-Methyl-3-(bicyclo[2.2.1]hept-2-yloxy)-4-methoxybenzyl alcohol

Following the procedure of Example 1B, from 3-(bicyclo[2.2.1]hept-2-yloxy)-4-methoxybenzaldehyde (8.53 mmol, 2.10 g) and methyllithium (25.58 mmol, 18.28 mL; 1.4M solution in ethyl ether) in dry tetrahydrofuran (80 mL) is obtained the crude alcohol. This material is purified by chromatography ($SiO_2$: methylene chloride) to give the title compound as a colorless oil (4.15 mmol, 1.09 g; 49%).

NMR (CDCl$_3$, 300 MHz) δ6.85 (m, 3H), 4.81 (q, 1H), 4.20 (d, J=5.0 Hz, 1H), 3.81 (s, 3H), 2.50 (d, J=5.0 Hz, 1H), 2.30 (s, 1H), 1.75 (m, 3H), 1.55 (m, 3H), 1.46 (d, 3H), 1.15 (m, 3H).

3-(Bicyclo[2.2.1]hept-2-yloxy)-4-methoxyacetophenone

Following the procedure of Example 1C, from α-methyl-3-(bicyclo[2.2.1]hept-2-yloxy)-4-methoxybenzyl alcohol (4.15 mmol, 1.09 g) and pyridinium dichromate (6.23 mmol, 2.34 g) in dry methylene chloride (50 mL) is obtained the ketone (3.42 mmol, 0.890 g; 82%) as a white solid of sufficient purity to be used as such without further purification.

NMR (DMSO-$d_6$, 300 MHz) δ7.60 (dd, J=8.5 Hz; 2.0 Hz, 1H), 7.27 (d, J=2.0 Hz, 1H), 7.02 (d, J=8.5 Hz, 1H), 4.25 (d, J=5.0 Hz, 1H), 3.80 (s, 3H), 2.50 (s, 3H), 2.35 (d, J=5.0 Hz, 1H), 2.25 (s, 1H), 1.85 (m, 1H), 1.45 (m, 4H), 1.13 (m, 3H).

D)

3-(Bicyclo[2.2.1]hept-2-yloxy)-4-methoxyacetophenone oxime

Following the procedure of Example 1D, from 3-(bicyclo[2.2.1]hept-2-yloxy)-4-methoxyacetophenone (3.42 mmol, 0.890 g) and hydroxylamine hydrochloride (3.76 mmol, 0.261 g) in dry pyridine (40 mL) is obtained the acetophenone oxime as a light yellow solid (3.01 mmol, 0.830 g; 88%) of sufficient purity to be used without further purification.

NMR (DMSO-$d_6$, 300 MHz) $\delta$11.0 (s, 1H), 7.20 (d, J=2.0 Hz, 1H), 7.14 (dd, J=8.5; 2.0 Hz, 1H), 6.93 (d, J=8.5 Hz, 1H), 4.20 (d, J=5.0 Hz, 1H), 3.75 (s, 3H), 2.35 (d, J=5.0 Hz, 1H), 2.25 (s, 1H), 2.10 (s, 3H), 1.71 (m, 1H), 1.50 (m, 4H), 1.15 (m, 3H).

E)

1-[3-(Bicyclo[2.2.1]hept-2-yloxy)-4-methoxyphenyl]ethanone (E)-O-(aminocarbonyl)oxime Following the procedure of Example 1E, to a slowly-stirred suspension of NaOCN (16.56 mmol, 1.08 g) in dry methylene chloride (20 mL) is added anhydrous trifluoroacetic acid (33.05 mmol, 3.78 g; 2.55 ml) and a solution of 3-(bicyclo[2.2.1]hept-2-yloxy)-4-methoxyacetophenone oxime (4.14 mmol, 1.14 g) in methylen chloride (20 mL) to obtain a yellow oil which is purified by flash chromatography ($SiO_2$: 1) 5% ethyl acetate/methylene chloride, 2) 8% ethyl acetate/methylene chloride, 3) 10% ethyl acetate/methylene chloride). The resulting white solid is dried in vacuo to afford analytically pure title compound (0.99 mmol, 0.316 g; 24%).

NMR (DMSO-$d_6$, 300 MHz) $\delta$7.35 (dd, J=8.5; 2.0 Hz, 1H), 7.34 (d, J=2.0 Hz, 1H), 7.08 (s, 2H), 6.98 (d, J=8.5 Hz, 1H), 4.36 (d, J=5.0 Hz, 1H), 3.79 (s, 3H), 2.32 (d, J=5.0 Hz, 1H), 2.29 (s, 3H), 2.26 (s, 1H), 1.74 (m, 1H), 1.59 (d, 1H), 1.43 (m, 3H), 1.33 (m, 3H).

IR (KBr) ($cm^{-1}$) 3480, 3280, 3220, 2950, 1750, 1720, 1515, 1350, 1252, 1140, 1000, 975.

MS (EI, m/e (%)) 318 ($M^-$, 10), 277 (17), 276 (100), 258 (99), 181 (14).

Analysis for: $C_{17}H_{22}N_2O_4$: Calculated: C, 64.13; H, 6.97; N, 8.80. Found: C, 63.96; H, 6.67; N, 8.66.

EXAMPLE 14

The following assay is employed to assess the ability of the compounds of the invention to inhibit PDE IV.

A solution containing PDE IV is prepared from canine tracheal muscle as follows:

The dog is euthanized with an overdose of beuthanasia while under anesthesia induced by a 33 mg/kg IV bolus of Nembutal. The trachealis muscle is removed, cleaned of connective tissue, and minced thoroughly. Three to four grams of tissue is then homogenized in Tris-HCl buffer (pH 7.8) using a Polytron. The homogenate is then centrifuged at 25,000×g (4° C.) for 30 minutes. The supernatant is decanted and filtered through four layers of gauze, and applied to a 40 cm×2 cm DEAE-Sepharose column that is equilibrated with Tris-HCl buffer (pH 7.8). The column is then washed with an additional 240 mL of buffer to remove unbound proteins. PDE is eluted using 450 mL of Tris-HCl buffer containing a linear gradient of 0.0–1.0M Na-acetate (80 mL/hr), and 7.5 mL fractions are collected. Each fraction is assayed for cAMP- and cGMP-metabolizing PDE activity. Fractions eluting at approximately 0.6M Na-acetate, and containing cAMP but not cGMP metabolic activity are pooled and used as a PDE stock solution for assaying PDE IV inhibitory activity.

PDE IV activity is assayed [as described in Thompson et al., *Advances in Cyclic Nucleotide Research*, 10, 69 (1979)] at 30° C. in a reaction mixture containing: 10 mM Tris-HCl (pH 7.8), 5 mM $MgCl_2$, 1 mM $\beta$-mercaptoethanol, 1 $\mu$M $^3$H-cAMP, 10 $\mu$M CI-930, PDE IV stock solution, and the desired concentration of test compound. CI-930 is included as an inhibitor of the cyclic GMP-sensitive, cyclic AMP-selective PDE (PDE III) that is also present in the PDE IV stock solution when prepared as described above. The ability of a test compound to inhibit PDE IV is determined by measuring the reduction in cAMP metabolism produced by the test compound and expressing it as a percentage of the reduction induced by 10 $\mu$M rolipram, a potent inhibitor of PDE IV [see Beavo, *Advances in Second Messenger and Phosphoprotein Research*, 22, 1 (1988)]. $IC_{50}$s are calculated for each test compound as the concentration of test compound that inhibits PDE IV by 50%.

When tested in this assay, the compounds of the invention give the following results.

TABLE 1

| Compound of Example No. | $IC_{50}$ of PDE IV |
|---|---|
| 1 | $4.8 \times 10^{-8}$ |
| 2 | $9.0 \times 10^{-8}$ |
| 3 | $4.1 \times 10^{-7}$ |
| 4 | $4.7 \times 10^{-8}$ |
| 5 | $2.5 \times 10^{-8}$ |
| 6 | $1.3 \times 10^{-7}$ |
| 7 | $1.2 \times 10^{-7}$ |
| 8 | $2.0 \times 10^{-7}$ |
| 9 | $1.5 \times 10^{-6}$ |
| 10 | $1.8 \times 10^{-7}$ |
| 11 | $2.4 \times 10^{-7}$ |
| 12 | $3.8 \times 10^{-7}$ |
| 13 | $6.7 \times 10^{-8}$ |

The compounds tested in this assay exhibit significant activity in inhibiting PDE IV.

What is claimed is:

1. A compound having the formula

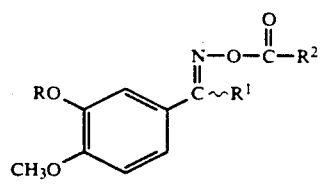

wherein
R is

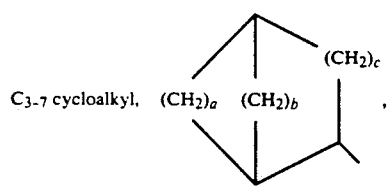

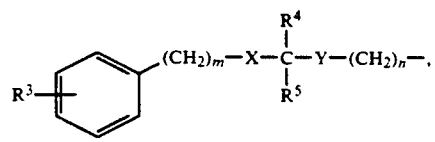

-continued

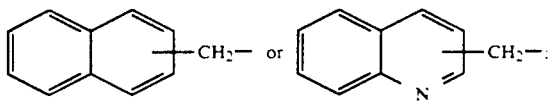

$R^1$ is hydrogen, lower alkyl or

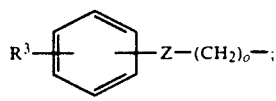

a is 1-3;
b is 1-3;
c is 0-2;
X, Y and Z are each, independently, a bond, O, S or NH, with the proviso that if one of X or Y is O, S or NH, the other must be a bond;
$R^2$ is amino, loweralkylamino, arylamino, loweralkoxy or aryloxy;
$R^3$ is hydrogen, halo, hydroxy, lower alkoxy, aryloxy, loweralkanoyloxy, amino, lower alkylamino, arylamino or loweralkanoylamino;
$R^4$ and $R^5$ are each, independently hydrogen or lower alkyl;
m is 0-4;
n is 1-4; and
o is 1-4.

2. The compound of claim 1, having the name 1-[3-(cyclopentyloxy)-4-methoxyphenyl]ethanone (E)-O-(aminocarbonyl)oxime.

3. The compound having the name 1-[3-(butoxy)-4-methoxyphenyl]ethanone (E)-O-(aminocarbonyl)oxime.

4. The compound of claim 1, having the name 1-[4-methoxy-3-(3-phenoxypropoxy)phenyl]ethanone (E)-O-(aminocarbonyl)oxime.

5. The compound of claim 1, having the name 1-(3-cyclopentyloxy-4-methoxyphenyl)-2-phenylethanone (E)-O-(aminocarbonyl)oxime.

6. The compound of claim 1, having the name 1-(3-cyclopentyloxy-4-methoxyphenyl)-3-phenylpropanone (E)-O-(aminocarbonyl)oxime.

7. The compound of claim 1, having the name 1-[3-(cyclopentyloxy)-4-methoxyphenyl]-3-methylbutanone (E)-O-(aminocarbonyl)oxime.

8. The compound of claim 1, having the name 1-[3-(cyclopentyloxy)-4-methoxyphenyl]ethanone (E)-O-[(methylamino)carbonyl]oxime.

9. The compound having the name 1-(3-butoxy-4-methoxyphenyl)ethanone (E)-O-[(methylamino)carbonyl]oxime.

10. The compound having the name 1-(3-butoxy-4-methoxyphenyl)ethanone (E)-O-[(phenylamino)carbonyl]oxime.

11. The compound of claim 1, having the name 1-(3-cyclopentyloxy)-4-methoxyphenyl]ethanone (E)-O-(methoxycarbonyl)oxime.

12. The compound having the name 1-(3-butoxy-4-methoxyphenyl)ethanone (E)-O-(methoxycarbonyl)oxime.

13. The compound having the name 1-(3-butoxy-4-methoxyphenyl)ethanone (E)-O-(phenoxycarbonyl)oxime.

14. The compound of claim 1, having the name 1-[3-(bicyclo[2.2.1]hept-2-yloxy)-4-methoxyphenyl]ethanone (E)-O-(aminocarbonyl)oxime.

* * * * *